(12) United States Patent
Chalfant et al.

(10) Patent No.: US 9,162,964 B2
(45) Date of Patent: Oct. 20, 2015

(54) ACRYLATE PRODUCTION PROCESS

(75) Inventors: David Chalfant, Levittown, PA (US);
Jeffery Goodwin, Deer Park, TX (US);
Dmitri A. Kraptchetov, Lansdale, PA (US); Robert Wilczynski, Yardley, PA (US)

(73) Assignee: Rohm and Haas Company

( * ) Notice: Subject to any disclaimer, the term of this patent is extended or adjusted under 35 U.S.C. 154(b) by 0 days.

(21) Appl. No.: 13/885,906

(22) PCT Filed: Nov. 7, 2011

(86) PCT No.: PCT/US2011/059517
§ 371 (c)(1),
(2), (4) Date: May 16, 2013

(87) PCT Pub. No.: WO2012/071158
PCT Pub. Date: May 31, 2012

(65) Prior Publication Data
US 2013/0245309 A1 Sep. 19, 2013

Related U.S. Application Data

(60) Provisional application No. 61/415,992, filed on Nov. 22, 2010.

(51) Int. Cl.
*C07C 67/08* (2006.01)
*C07C 67/54* (2006.01)

(52) U.S. Cl.
CPC ............... *C07C 67/08* (2013.01); *C07C 67/54* (2013.01)

(58) Field of Classification Search
CPC .................................. C07C 67/08; C07C 67/54
USPC .......................................................... 560/205
See application file for complete search history.

(56) References Cited

U.S. PATENT DOCUMENTS

| | | | |
|---|---|---|---|
| 3,426,040 A * | 2/1969 | Langecker | ..................... 549/368 |
| 4,012,439 A | 3/1977 | Erpenbach et al. | |
| 4,280,010 A | 7/1981 | Erpenbach et al. | |
| 5,734,074 A | 3/1998 | Dockner et al. | |
| 5,877,345 A | 3/1999 | Bauer, Jr. et al. | |
| 6,172,258 B1 | 1/2001 | Jawaid et al. | |
| 6,180,819 B1 | 1/2001 | Bauer, Jr. et al. | |
| 6,180,820 B1 | 1/2001 | Jawaid et al. | |
| 6,472,554 B1 | 10/2002 | Deckert et al. | |
| 6,506,930 B1 | 1/2003 | Venter et al. | |
| 7,569,721 B2 | 8/2009 | Patterson et al. | |
| 2006/0205972 A1 | 9/2006 | Clymo et al. | |
| 2006/0205973 A1 | 9/2006 | Habeck et al. | |

FOREIGN PATENT DOCUMENTS

| | | | |
|---|---|---|---|
| EP | 1215194 | * 11/2001 | ............. C07C 67/08 |
| EP | 779268 | 6/2002 | |
| EP | 1215194 | 6/2002 | |
| EP | 1182189 | 3/2005 | |

OTHER PUBLICATIONS

Coker, Ludwig's Applied Process Design for Chemical and Petrochemical Plants, vol. 2 (4th Ed.), Elsevier, p. 165-166 and 228-230, 2010.*
Richardson, J.F. Harker, J.H. Backhurst, J.R. (2002). Coulson and Richardson's Chemical Engineering vol. 2—Particle Technology and Separation Processes (5th Edition). Elsevier.*
Sinnott, R.K. (2005). Coulson and Richardson's Chemical Engineering vol. 6—Chemical Engineering Design (4th Edition). Elsevier.*

* cited by examiner

*Primary Examiner* — Paul A Zucker
*Assistant Examiner* — Mark Luderer

(57) ABSTRACT

A process comprising for preparing $C_1$ to $C_4$ alkyl(meth)acrylates, such as butyl acrylate, wherein vaporized reactor contents are fed directly to a column, the aqueous reflux ratio to the column is from 4 to 12, and the level of acrylic acid in the primarily organic phase separated from the overhead condensate of the column is less than 2000 ppm.

19 Claims, 1 Drawing Sheet

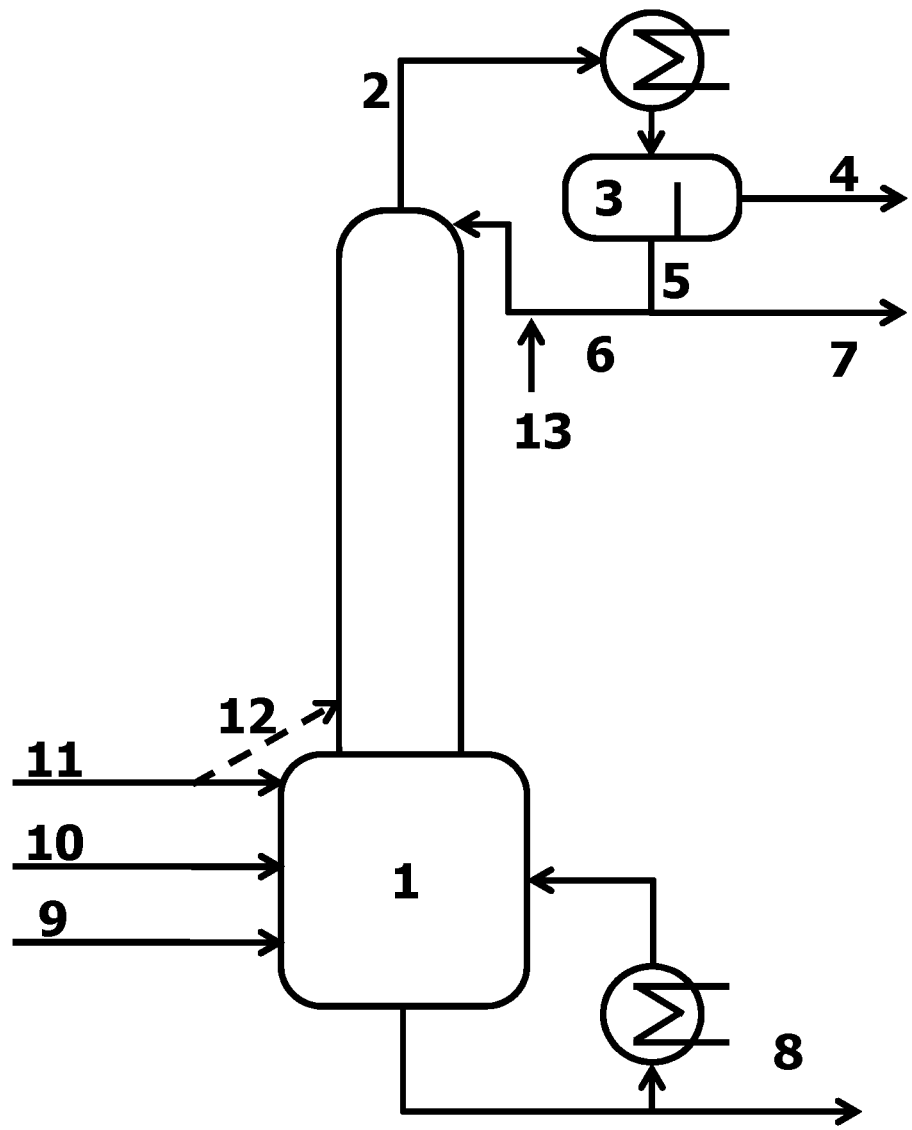

ACRYLATE PRODUCTION PROCESS

CROSS-REFERENCE TO RELATED APPLICATIONS

This application claims priority from provisional application Ser. No. 61/415,992, filed Nov. 22, 2010, which is incorporated herein by reference in its entirety.

BACKGROUND OF THE INVENTION

This invention relates to a process for preparing alkyl (meth)acrylates.

Distillation is commonly used in butyl acrylate (BA) production. For example, U.S. Pat. No. 4,012,439 ('439) describes a continuous acrylic acid alkyl ester ("alkyl acrylate") process in which an esterification mixture produced in a standalone reactor is distilled through an acrylic acid (AA) separation column to give an overhead mixture of alkyl acrylate, butanol, and water, and, from the column bottom, a concentrated AA stream that is returned to the reactor. While separating the overhead mixture from AA, the '439 process recycles a very high proportion (about 97%) of aqueous phase distillate to the head of the AA-separating column. This high proportion of aqueous recycle (i.e. an aqueous reflux ratio of about 32:1) disadvantageously requires a large column and a large expenditure of energy due to the large volumes of water returned to the process.

U.S. Pat. No. 6,180,819 ('819) describes a continuous process for producing alkyl acrylate in which a reactor esterification mixture produced in a standalone reactor is first condensed, then distilled through an AA separation column to give an overhead mixture of alkyl acrylate, butanol, and water, and, from the column bottom, a concentrated AA stream that is returned to the reactor. To separate the overhead mixture from AA and achieve overhead mixture of alkyl acrylate that is substantially free of AA (<2,000 ppm), the '819 process in one embodiment employs a high aqueous reflux ratio of at least 8.5 to the head of the AA-separating column. In fact, '819 demonstrates that using aqueous reflux ratios below 8.5, such as 6.3, leads to an undesirable organic operating state in the AA-separating column characterized by the loss of AA/alkyl acrylate separation where a concentration of AA in the overhead mixture of alkyl acrylate is at least an order of magnitude larger than the maximum of 2,000 ppm AA achieved at reflux ratios of 8.5 and above. Although a substantial improvement over the aqueous reflux ratio of 32 described in '439, the '819 process limit of aqueous reflux ratio of 8.5 disadvantageously requires a large column and a large expenditure of energy associated with returning large volumes of water to the process. Furthermore, the intermediate condensation of the reactor vapor, as well as the use of the standalone reactor and AA-separating column in '819 disadvantageously requires a large capital expenditure for multiple pieces of equipment.

A second embodiment of the '819 process is described wherein esterification mixture vapor is fed directly from the reactor to the AA-separating column, eliminating the need for intermediate condensation of the reactor esterification mixture. However, this embodiment of the '819 process requires an aqueous reflux ratio of at least 13 in order to maintain the desired aqueous operating mode in the AA-separating column to produce overhead mixture of alkyl acrylate that is substantially free of AA (<2,000 ppm). The increased aqueous reflux ratio requirement in this second embodiment of the '819 process, again, disadvantageously requires a large column and a large expenditure of energy due to the large volumes of water returned to the process.

Thus, in the production of alkyl acrylates, there remain problems concerning significant energy use and high capital expenditure. There is a need for a process that would efficiently use the water of reaction in facilitating distillative separation of acrylic ester from AA, particularly with reduced energy use. In addition, there is need for a process for production of acrylates with reduced capital requirements. Meeting one or more of these needs would provide increases in process and/or material use efficiencies.

SUMMARY OF THE INVENTION

The invention is a process comprising: (A) feeding a $C_1$ to $C_4$ alcohol, a (meth)acrylic acid, a catalyst, and optionally water to a reactor; (B) subjecting the components of step (A) to reaction conditions in the reactor to produce a $C_1$ to $C_4$ alkyl (meth)acrylate and water; (C) feeding vaporized $C_1$ to $C_4$ alkyl (meth)acrylate, alcohol and water from the reactor directly to a distillation column; (D) withdrawing an overhead stream from the column, the stream comprising a $C_1$ to $C_4$ alkyl (meth)acrylate product, alcohol and water; (E) condensing the overhead stream from the column to form a condensed overhead stream; (F) separating the condensed overhead stream to form a primarily aqueous phase and a primarily organic phase; (G) sending the primarily organic phase to a product purification process; and (H) refluxing at least part of the primarily aqueous phase to the column, with the proviso that the aqueous reflux ratio is from 4 to 12, and the level of acrylic acid in the primarily organic phase is less than 2000 ppm.

Surprisingly, the process demonstrates good separation of AA from the (meth)acrylate-rich organic distillate despite the low aqueous reflux ratio employed.

BRIEF DESCRIPTION OF THE DRAWINGS

FIG. 1 is a process schematic diagram.

DETAILED DESCRIPTION OF THE INVENTION

The process of this disclosure employs a $C_1$ to $C_4$ alcohol; a (meth)acrylic acid; a catalyst, and optionally water, as starting materials.

For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges by endpoints include all numbers subsumed in that range (e.g., 1 to 5 includes 1, 1.5, 2, 2.75, 3, 3.80, 4, 5, etc.).

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes "a" hydrophobic polymer can be interpreted to mean that the composition includes "one or more" hydrophobic polymers.

Abbreviations used herein include; BA=butyl acrylate; AA=acrylic acid; BuOH=butanol; 4-hydroxy 2,2,6,6-tetramethyl-1-piperidinyloxy free radical=4HT; the mono-methyl ether of hydroquinone=MeHQ.

As used herein, the term "(meth)acrylic" acid is meant to include both acrylic acid and methacrylic acid. In a like manner, the term "(meth)acrylate" is meant to include both acrylate and methacrylate.

As used herein, BuOH refers to n-butanol, i.e., 1-butanol and the term "butanol" includes within its scope all butanol isomers as well as mixtures thereof.

The term "alkyl" is meant to include branched chain, straight chain or cyclic alkyl groups.

As used herein, the terms "AA rich" or "BA rich" are understood to mean fractions or components where AA or BA is the major (for example, greater than 50% by weight) organic component of the composition.

As used herein, the term "aqueous reflux ratio" is defined as the weight of aqueous phase refluxed, i.e. returned to the column, to the weight of aqueous phase not refluxed, i.e. taken forward.

Throughout this specification and claims, unless otherwise indicated, references to percentages are by weight, all temperatures by degree centigrade and all pressures are absolute, not gauge.

FIG. 1 illustrates the equipment and the flow lines utilized in one embodiment of the process of the present invention, including the direct esterification reactor 1, which is a stirred reactor with a distillation column mounted on top of it; line 2, which carries a vaporized distillate mixture, which includes BA, from 1 to the condenser of a phase separator 3, the phase separator 3 separates the condensed distillate into a BA rich organic phase and an aqueous distillate phase; line 4, which carries the BA rich organic distillate separated in 3 forward to a product purification section; line 5, which carries the aqueous distillate separated in 3 to line 6 to be recycled to 1, and to line 7 to carry the rest of it forward to be treated, generally to recover material from aqueous waste; line 8, which carries the bottoms from 1 to a heavies recovery section, generally to recover values for recycling via at least one of lines 11 or 12. Line 9 supplies catalyst to the reactor. Line 10 supplies fresh AA and BuOH to the reactor. Line 11 carries the BuOH, BA, and AA recovered in the product purification and heavies recovery sections from lines 4, 7 and 8 back to the reactor 1; and optional line 12 returns all or part of recovered material to an alternative feed location for reactor 1, such as the column. Line 13 may carry inhibitor to one or more locations in reactor 1.

As recited above, in step (A) of the present invention $C_1$ to $C_4$ alcohol, a (meth) acrylic acid, a catalyst, and water are charged to a reactor to form a reaction mixture. Many examples of these materials are widely commercially available or can be readily synthesized by those skilled in the art using known methods.

Generally, the $C_1$ to $C_4$ alcohol is a branched or straight chain alkanol having 1 to 4 carbon atoms or mixture thereof. Specific examples include, but are not limited to, methanol, ethanol, n-propanol, isopropanol, n-butanol, 2-butanol, tert-butanol or mixtures thereof. Furthermore, it is contemplated that the $C_1$ to $C_4$ alcohol may be substituted, for example, with halogen, hydroxide, alkoxide, cyano, nitro, etc. In one embodiment, the alcohol is butanol. In a preferred embodiment, the alcohol is n-butanol.

The reaction mixture may also contain (meth)acrylic acid substituted, for example, with halogen, hydroxide, alkoxide, cyano, nitro, etc. In one embodiment, acrylic acid or methacrylic acid or a mixture thereof is present. In a preferred embodiment, the unsaturated acid is acrylic acid. The (meth) acrylic acid and alcohol advantageously are fed to the esterification reactor in a molar ratio of 1:1 to 1:1.7, preferably 1:1.4 to 1:1.6. It is also contemplated that other unsaturated acids such as crotonic acid, cinnamic acid, maleic acid, fumaric acid, etc., which can participate in an esterification reaction with an alcohol, may be utilized in the process of the present invention. In one embodiment, the purity of the (meth)acrylic acid is not particularly critical, e.g. the (meth) acrylic acid can include crude (meth)acrylic acid or higher grades of (meth)acrylic acid.

An acidic catalyst is also present in the reaction mixture. Preferably, the catalyst is a strong acid catalyst. Suitable examples of the catalyst include, but are not limited to, sulfuric acid, methane sulfonic acid, benzene sulfonic acid, p-toluene sulfonic acid, mixtures thereof, or a polymer supported alkyl sulfonic acid such as AMBERLYST™ 15 resin or NAFION-H™ resin. Generally, the alkyl sulfonic acid is a $C_1$ to $C_{10}$ alkyl sulfonic acid. In one embodiment, the strong acid catalyst is a sulfur containing acid or sulfur containing polymer supported acid. In a preferred embodiment, the strong acid catalyst is sulfuric acid. Salts of such acids, such as for example, $NaHSO_4$, $KHSO_4$, $Fe(HSO_4)_2$, and $Fe(HSO_4)_3$, may also be employed as the catalyst. The concentration of catalyst by total weight of the reaction mixture in the direct esterification reactor is typically from 0.5 to 15% by weight, preferably from 1 to 12% by weight, and more preferably from 2 to 8% by weight. In one embodiment, the amount of catalyst is from 1 to less than 5% by weight.

Water can also be present in the reaction mixture provided in step (A). Generally, any water, such as tap water, distilled water or deionized water, suitable for use in a direct esterification reaction, may be used. Some or all of the water provided may be water of reaction that is produced during the reaction. Furthermore, at least some of the water provided may be recycled water of reaction that has been removed during separation of the reaction product from the starting materials. The water provides a portion of the reaction medium in the reactor. The level of liquid water in the reaction zone advantageously is from 1 to 6% by weight, based on the weight of the liquid in the reactor. In one embodiment, the level of liquid water in the reaction zone is from 2 to 4% by weight.

At least one inhibitor may also be charged to the reactor in step (A) or added elsewhere in the process. Inhibitor, if used, may be fed to multiple locations in the process, as is known to those skilled in the art. Typically, from 0.001 to 1.0%, preferably from 0.001 to 0.5%, and more preferably from 0.001 to 0.1%, based on the total weight of the reaction mixture, of at least one inhibitor is present during the direct esterification process to prevent polymerization. Examples of suitable inhibitors include hydroquinone, the mono-methyl ether of hydroquinone (MeHQ), phenothiazine, 2,2,6,6-tetramethyl-1-piperidinyloxy free radical (TEMPO), 4-hydroxy-2,2,6,6-tetramethyl-1-piperidinyloxy free radical (4HT), butylated hydroxy anisole, naphthoquinone, anthranil. Derivatives of these inhibitors may also be used. Such derivatives include, but are not limited to 4-methacryloyloxy-2,2,6,6-tetramethyl piperidinyl free radical and 4-hydroxy-2,2,6,6-tetramethyl N-hydroxy piperidine. In a preferred embodiment, at least one inhibitor is 4HT. In another embodiment, at least one inhibitor is TEMPO. In another embodiment, 4HT and another inhibitor, such as MeHQ are employed. It is also recognized that the acrylic acid used as part of the feed typically contains inhibitors as well. These inhibitors include, for example, phenothiazine, hydroquinone, MeHQ, and copper dibutyldithiocarbamate. Combinations of inhibitors can be employed.

In one embodiment, the alcohol is butanol, the (meth)acrylic acid is acrylic acid, and the catalyst is sulfuric acid.

The present invention advantageously utilizes one reactor wherein direct esterification of AA and BuOH is achieved. Generally, any reactor suitable or adaptable for a direct esterification reaction process may be employed. The reactor advantageously has means for removing a bottoms stream. In one embodiment, the reactor may be a stirred tank equipped with a distillation column. The reactor can include means for feeding AA, BuOH, a catalyst, water, and at least one inhibitor. Optionally, a pre-reactor can be employed.

In step (B) the reaction mixture reacts to form a $C_1$ to $C_4$ alkyl (meth)acrylate and reaction byproducts.

The direct esterification reaction may be run by feeding AA and BuOH to the direct esterification/reactor in an AA to BuOH molar ratio ranging from 1:1 to 1:1.7, preferably 1:1.4 to 1:1.6. The AA, BuOH, inhibitor, catalyst, and water form a reaction mixture in the direct esterification reactor. In one embodiment, the AA and BuOH are reacted to a conversion on AA of from 60 to 99%, and in another embodiment the AA conversion is from 90 to 99%. Generally speaking, higher conversions are preferred in order to produce BA that is substantially free of AA, i.e. less than 2,000 ppm AA.

The direct esterification reaction is run at a temperature of from 90° C. to 120° C., preferably 95° C. to 110° C., and more preferably 98° C. to 105° C. In one embodiment, the direct esterification reaction is run at a temperature of from 90° C. to 99° C. The direct esterification reaction is run at pressures from 100 mm Hg (13.3 kPa) to 760 mm Hg (101 kPa). In one embodiment, the reaction pressure is from 100 (13.3 kPa) to 400 mm Hg (53.3 kPa). The residence time in the direct esterification reactor is typically from 0.25 to 5 hours, preferably from 0.5 to 3 hours, and more preferably from 0.5 to 2 hours.

In a preferred embodiment, the distillation column is situated directly on top of the reactor, i.e. mounted on the reactor, (as in FIG. 1) and may be a fractional distillation column. The column may contain trays or packing. Advantageously, the column contains a number of trays sufficient to achieve the desired separation. Design of distillation columns is well known to those skilled in the art. In one embodiment, the distillation column contains from 20 to 100 trays. In other embodiments, the column contains from 30 to 70 trays, or from 40 to 50 trays. In one embodiment, the column contains sieve trays, with or without downcomers. The column may be a divided wall column or any other conventional column design. The reactor can include means for feeding AA, BuOH, a catalyst, water, and at least one inhibitor directly to the reactor and/or to the column section.

The $C_1$ to $C_4$ alkyl (meth)acrylate and water formed during the reaction of the alcohol with the (meth)acrylic acid are separated from the reaction mixture by methods known in the art such as distillation, phase separation, etc. In a preferred embodiment, the $C_1$ to $C_4$ alkyl (meth)acrylate and water formed during the reaction are separated from the reaction mixture by azeotropic distillation. In a more preferred embodiment, i.e. in the production of BA, BA is azeotropically distilled with water (aqueous reflux) and BuOH under the conditions described above, up through the column on top of the reactor. Accordingly, the water added to the column as reflux provides an aqueous medium within the effluent passing up the column, which enhances separation of AA and BA in the distillation column The distillate may then be taken through line 2 to a phase separator 3. In the phase separator, an organic phase that is BA rich and contains BuOH, and an aqueous phase that contains water and AA, separate. The organic phase may be taken through line 4 to a product purification section, wherein BA of the desired purity is obtained. BuOH may be recovered from the product purification section and recycled. Part of the aqueous phase is taken through line 5 to line 6 to be recycled to the column to maintain the appropriate amount of water in the column. The rest of the aqueous phase is taken through line 5 to line 7 to carry it forward to be recovered and treated, generally as waste.

In one embodiment, substantially 100% of the primarily organic phase is fed to further separation steps, i.e. is not refluxed to the distillation column. The aqueous reflux ratio advantageously is set to allow the overhead BA mixture to be substantially free of AA. In various embodiments, the aqueous reflux ratio is from 4 to 12, is from 5 to 11, or is from 5.5 to 8.

SPECIFIC EMBODIMENTS OF THE INVENTION

The following examples illustrate the process of the present invention.

Materials: AA, BA, and BuOH are obtained from plant production streams. The inhibitors used are commercially available.

Analyses: Standard methods are used for determination of water, monomer, BuOH, and residual impurities. Sulfuric acid determinations are obtained using a pH probe and alcoholic tetrabutylammonium hydroxide titrant. Water was determined using a Karl Fisher titration unit.

The following examples are given to illustrate the invention and should not be construed as limiting its scope. All parts and percentages are by weight unless otherwise indicated.

Example 1

Preparation of Butyl Acrylate

A direct esterification reactor is set up using a 5,000 ml round bottom flask connected with a multi-tube zirconium steam-jacketed thermosiphon reboiler. A glass 45 tray, 5.08 cm Oldershaw fractional distillation column is affixed directly on top of the glass reactor. An overhead system of two 316 SS, chilled water cooled condensers arranged in series is affixed to the fractional distillation column. A 500 ml jacketed, chilled, glass fraction cutter is situated following the condenser. A differential vacuum arrangement including a graduated fraction cutter with a Teflon stopcock is used for collecting the bottoms stream from the reactor.

AA, BuOH, and sulfuric acid are fed to the direct esterification reactor. The feed stream also includes BA, water, butyl acetate, and dibutyl ether to simulate components typical of a butyl acrylate process with recycle from downstream units. Direct esterification reactor operating conditions of 100° C. and 295 mm Hg (39.3 kPa) are targeted. Inhibitor consisting of 0.11 wt % 4HT and 74 ppm of MeHQ in BA is pumped to the condenser series at the rate of 7 g/hr. Inhibitor consisting of 0.32 wt % 4HT and 222 ppm MeHQ in BA is pumped to the top of the fractional distillation column at the rate of 10 g/hr. Once the top trays of the fractional distillation column are wetted with inhibitor solution, steam is introduced to the reboiler. When distillate is observed in the overhead system, the following feed mixture is delivered into the reactor via positive displacement FMI piston pump: 493.7 g/hr total AA (including recycle), 784.3 g/hr total BuOH (including recycle), 36 g/hr total water (including recycle), 119.5 g/hr BA (recycle), 3 g/h butyl acetate (recycle), 2.4 g/hr dibutyl ether (recycle). Additionally, 4.8 g/hr sulfuric acid is delivered into the reactor via a peristaltic pump using appropriate tubing compatible with strong mineral acid. The feed residence time in the reactor and reboiler circulation loop, combined, is 70 minutes. Distillate and bottoms streams are collected half-hourly and thoroughly analyzed in combined two-hour composite cuts. The unit is operated continuously until steady state is achieved, as indicated by stabilized flow rates and composition profiles. The distillate separates into two layers, which are isolated by using a separatory funnel. The organic (top) distillate layer, containing primarily BA, is collected as organic overhead product in its entirety (i.e., none is refluxed to the column). The aqueous (bottom) distillate layer is partially returned to the top tray of the column as aqueous reflux at the rate of 676 g/hr. The remaining aqueous distillate layer is collected as the aqueous overhead stream at the rate of 103 g/hr. The aqueous reflux ratio is calculated as (676/103)= 6.6.

A bottoms stream is withdrawn from the direct esterification reactor at the rate of 115 g/hr. The reactor-column process has a molar BA yield of 98% based on neat AA, i.e., after accounting for the presence of 4 wt % of acrylic acid dimer in the AA feed. The reactor-column process has a molar BA yield of 61% based on BuOH. The yield of BA based on BuOH appears reduced because the feed includes an excess of BuOH, making AA the limiting reagent. Note that the above molar BA yields are measured solely around the reactor-column system described. In a typical BA process, values are recovered both from the reactor bottoms and overhead distillate streams and recycled to the reactor section. It is therefore not uncommon for molar BA yields on AA and BuOH for the overall BA process to approach quantitative, depending on the quality of value recovery and recycle.

The overhead mixture of BA is substantially free of AA, with AA levels in the organic distillate being <1000 ppm. Surprisingly, the process demonstrates impressive separation of AA from the BA-rich organic distillate, despite the low aqueous reflux ratio of 6.6 that is used.

Example 2

Preparation of Butyl Acrylate at Lower Molar Excess of BuOH

Example 1 is repeated, except that a lower molar excess of BuOH in the feed is used, i.e., molar ratio of AA to BuOH of 1:1.36, and with the following other differences. The inhibitor consisting of 0.11 wt % 4HT and 74 ppm of MeHQ in BA is pumped to the condenser series at the rate of 6 g/hr. The inhibitor consisting of 0.32 wt % 4HT and 222 ppm MeHQ in BA is pumped to the top of the fractional distillation column at the rate of 11 g/hr. The following feed mixture is delivered into the reactor: 538.0 g/hr total AA (including recycle), 752.7 g/hr total BuOH (including recycle), 32.3 g/hr total water (including recycle), 111.0 g/hr BA (recycle), 3.5 g/h butyl acetate (recycle), 2.4 g/hr dibutyl ether (recycle). Additionally, 6.7 g/hr sulfuric acid is delivered into the reactor. The aqueous distillate layer is collected as the aqueous overhead stream at the rate of 118 g/hr. The aqueous reflux ratio is calculated as (676/118)=5.7.

A bottoms stream is withdrawn from the direct esterification reactor at the rate of 152 g/hr. The reactor-column process has a molar BA yield of 95% based on neat AA, i.e., after accounting for the presence of 3.2 wt % of acrylic acid dimer in the AA feed. The reactor-column process has a molar BA yield of 68% based on BuOH. The overhead mixture of BA is substantially free of AA, with AA levels in organic distillate being <2000 ppm.

Example 3

Preparation of Butyl Acrylate at Lower Residence Time

Example 1 is repeated, except that a lower feed residence time of 33 minutes is used, and with the following other differences. The inhibitor consisting of 0.32 wt % 4HT and 222 ppm MeHQ in BA is pumped to the top of the fractional distillation column at the rate of 9 g/hr. The following feed mixture is delivered into the reactor: 494.1 g/hr total AA (including recycle), 784.2 g/hr total BuOH (including recycle), 36.0 g/hr total water (including recycle), 117.6 g/hr BA (recycle), 2.7 g/hr butyl acetate (recycle), 2.4 g/hr dibutyl ether (recycle). Additionally, 6.1 g/hr sulfuric acid is delivered into the reactor. The feed residence time in the reactor and reboiler circulation loop, combined, is 33 minutes. The aqueous (bottom) distillate layer is partially returned to the top tray of the column as aqueous reflux at the rate of 668 g/hr. The remaining aqueous distillate layer is collected as the aqueous overhead stream at the rate of 100 g/hr. Correspondingly, the aqueous reflux ratio is (668/100) or 6.7.

A bottoms stream is withdrawn from the direct esterification reactor at the rate of 139 g/hr. The reactor-column process has a molar BA yield of 97% based on neat AA, i.e., after accounting for the presence of 4.7 wt % of acrylic acid dimer in the AA feed. The reactor-column process has a molar BA yield of 60% based on BuOH. The overhead mixture of BA is substantially free of AA, with AA levels in organic distillate being <1000 ppm.

These examples demonstrate that the process of this invention is effective at producing alkyl (meth)acrylates by direct esterification efficiently and economically.

Specifically:
(1) the direct esterification reaction and the separation of acrylate product from AA starting material occurs in a single reactor-column unit, without the need for intermediate condensation of the reactor product vapor
(2) the separation of acrylate product from AA starting material successfully occurs at unexpectedly low aqueous reflux ratios, without the onset of an undesirable organic steady state.

What is claimed is:
1. A process for preparing butyl acrylate, the process comprising: (A) feeding butyl alcohol, acrylic acid, a catalyst, and optionally water to a reactor; (B) subjecting the components of step (A) to reaction conditions in the reactor to produce butyl acrylate and water; (C) feeding vaporized butyl acrylate, butyl alcohol and water from the reactor directly to a distillation column, and separating the butyl acrylate and water formed during the reaction from the reaction mixture by azeotropic distillation; (D) withdrawing an overhead stream from the column, the stream comprising a butyl acrylate product, butyl alcohol and water; (E) condensing the overhead stream from the column to form a condensed overhead stream; (F) separating the condensed overhead stream to form a primarily aqueous phase and a primarily organic phase; (G) sending the primarily organic phase to a product purification process; and (H) refluxing at least part of the primarily aqueous phase to the column, with the proviso that the aqueous reflux ratio is from 5 to 8, and the level of acrylic acid in the primarily organic phase is less than 2000 ppm.

2. The process of claim 1 wherein 100% of the primarily organic phase is fed to further separation steps.

3. The process of claim 1 wherein the column possesses a minimum of 25 trays.

4. The process of claim 1 wherein the catalyst is a strong acid catalyst.

5. The process of claim 1 wherein the level of acrylic acid in the primarily organic phase is less than 1000 ppm.

6. The process of claim 1 wherein the vaporized butyl acrylate, butyl alcohol and water from the reactor are fed to the bottom of the distillation column.

7. The process of claim 1 wherein the level of catalyst in the reactor is from 1 to less than 5% by weight based on the weight of the liquid in the reactor.

8. The process of claim 1 wherein the pressure in the reactor is from 100 mm Hg (13.3 kPa) to 760 mm Hg (101 kPa).

9. The process of claim 1 wherein the ratio of acrylic acid to butanol fed to the reactor is from 1:1 to 1:1.7.

10. The process of claim 1 wherein the aqueous reflux ratio is from 5.5 to 8.

11. The process of claim 1 wherein the catalyst is a strong acid catalyst, the level of acrylic acid in the primarily organic phase is less than 2000 ppm, and the level of catalyst in the reactor is from 1 to less than 5% by weight based on the weight of the liquid in the reactor.

12. The process of claim 1 wherein the process is continuous, the distillation column is mounted on the reactor, and the amount of water in the reactor is from 2 to 4 weight percent based on the weight of liquid in the reactor.

13. A process for preparing butyl acrylate, the process comprising: (A) feeding butyl alcohol, acrylic acid, a catalyst, and optionally water and at least one polymerization inhibitor to a device; (B) subjecting the components of step (A) to reaction conditions in a reactor to produce butyl acrylate and water; (C) feeding vaporized butyl acrylate, alcohol and water from the reactor directly to a distillation column; (D) withdrawing an overhead stream from the column, the stream comprising butyl acrylate product, alcohol and water; (E) condensing the overhead stream from the column to form a condensed overhead stream; (F) separating the condensed overhead stream to form a primarily aqueous phase and a primarily organic phase; (G) sending the primarily organic phase to a product purification process; and (H) refluxing at least part of the primarily aqueous phase to the column, with the proviso that the aqueous reflux ratio is from 5 to 8, the level of acrylic acid in the primarily organic phase is less than 2000 ppm, and the device comprises either or both of the reactor and the distillation column.

14. The process of claim 1 wherein the feeding vaporized butyl acrylate, butyl alcohol and water from the reactor directly to a distillation column is accomplished by feeding the vaporized butyl acrylate, butyl alcohol and water from the reactor directly to the bottom of a distillation column.

15. A process for preparing butyl acrylate, the process comprising: (A) feeding butyl alcohol, acrylic acid, a catalyst, and optionally water to a reactor; (B) subjecting the components of step (A) to reaction conditions in the reactor to produce butyl acrylate and water; (C) feeding vaporized butyl acrylate, butyl alcohol and water from the reactor to a distillation column that is mounted on the reactor, and separating the butyl acrylate and water formed during the reaction from the reaction mixture by azeotropic distillation; (D) withdrawing an overhead stream from the column, the stream comprising a butyl acrylate product, butyl alcohol and water; (E) condensing the overhead stream from the column to form a condensed overhead stream; (F) separating the condensed overhead stream to form a primarily aqueous phase and a primarily organic phase; (G) sending the primarily organic phase to a product purification process; and (H) refluxing at least part of the primarily aqueous phase to the column, with the proviso that the aqueous reflux ratio is from 5 to 8, and the level of acrylic acid in the primarily organic phase is less than 2000 ppm.

16. The process of claim 15 wherein the process is continuous.

17. The process of claim 15 wherein the level of acrylic acid in the primarily organic phase is less than 1000 ppm.

18. The process of claim 15 wherein the aqueous reflux ratio is from 5.5 to 8.

19. The process of claim 16 wherein the catalyst is a strong acid catalyst.

* * * * *